United States Patent
Yeh et al.

(10) Patent No.: US 11,925,916 B2
(45) Date of Patent: Mar. 12, 2024

(54) METHOD AND COMPOSITION FOR REMOVING UREMIC TOXINS

(71) Applicants: BAXTER INTERNATIONAL INC., Deerfield, IL (US); BAXTER HEALTHCARE S A, Glattpark (CH)

(72) Inventors: Rosa Hung-Chen Yeh, Libertyville, IL (US); Yuanpang Samuel Ding, Long Grove, IL (US); Cristian Adolfo Menzel Bueno, Gurnee, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 848 days.

(21) Appl. No.: 16/203,058

(22) Filed: Nov. 28, 2018

(65) Prior Publication Data

US 2020/0164339 A1    May 28, 2020

(51) Int. Cl.
    *B01J 20/02*    (2006.01)
    *A61M 1/16*     (2006.01)
    *A61M 1/28*     (2006.01)

(52) U.S. Cl.
    CPC ........ *B01J 20/0211* (2013.01); *A61M 1/1696* (2013.01); *A61M 1/284* (2014.02)

(58) Field of Classification Search
    CPC ................ A61M 1/1696; B01J 20/0211
    See application file for complete search history.

(56) References Cited

U.S. PATENT DOCUMENTS

| | | | |
|---|---|---|---|
| 4,391,964 A | 7/1983 | Wick et al. | |
| 4,623,329 A | 11/1986 | Drobish et al. | |
| 5,587,157 A * | 12/1996 | Cox | A61L 9/01 252/175 |
| 6,332,985 B1 | 12/2001 | Sherman et al. | |
| 9,682,184 B2 | 6/2017 | Wong | |
| 9,707,329 B2 | 7/2017 | Merchant et al. | |
| 2004/0191162 A1 | 9/2004 | Hai et al. | |
| 2013/0123560 A1 | 5/2013 | Jacobson et al. | |
| 2013/0260988 A1 | 10/2013 | Herfert et al. | |
| 2014/0001112 A1 | 1/2014 | Karoor et al. | |
| 2014/0336568 A1 * | 11/2014 | Wong | A61M 1/287 604/29 |
| 2015/0108069 A1 | 4/2015 | Merchant et al. | |
| 2015/0251162 A1 | 9/2015 | Pudil et al. | |
| 2015/0367055 A1 | 12/2015 | Pudil et al. | |
| 2016/0243299 A1 | 8/2016 | Martin | |
| 2016/0243541 A1 | 8/2016 | Menon et al. | |
| 2018/0030604 A1 | 2/2018 | Manabe et al. | |
| 2018/0177933 A1 | 6/2018 | Merchant | |
| 2018/0214623 A1 | 8/2018 | Martin | |
| 2020/0164128 A1 | 5/2020 | Ding et al. | |

FOREIGN PATENT DOCUMENTS

| | | |
|---|---|---|
| CN | 104039439 | 9/2014 |
| EP | 0311244 | 4/1989 |
| EP | 3269757 | 1/2018 |
| EP | 3326712 | 5/2018 |
| EP | 3415182 | 12/2018 |
| EP | 3546042 | 10/2019 |
| JP | S48-088192 | 11/1973 |
| JP | 2006-519299 | 8/2006 |
| RU | 2137540 | 9/1999 |
| RU | 2401160 | 10/2010 |
| WO | 2003/042098 | 5/2003 |
| WO | 2009/157877 | 12/2009 |
| WO | 2011/125758 | 10/2011 |
| WO | 2015/060914 | 4/2015 |
| WO | 2015/199768 | 12/2015 |
| WO | 2015/199864 | 12/2015 |
| WO | 2016/191042 | 12/2016 |

OTHER PUBLICATIONS

T Li, Langmuir, (1997), v13, p. 3570-3574.*
Written Opinion dated Oct. 7, 2020 for PCT/US2019/063664 (7 pages).
Transmittal of International Search Report and Written Opinion of the International Searching Authority for PCT/US2019/063699 dated Mar. 13, 2020 (19 pages).
IPRP for PCT/US2019/063664 dated Feb. 16, 2021 (17 pages).
Transmittal of International Search Report and Written Opinion of the International Searching Authority for PCT/US2019/063664 dated Feb. 21, 2020 (13 pages).
Japanese Office Action dated Feb. 7, 2023 for App. No. P2021-529042.
India Office Action dated Jan. 20, 2023 for App. No. 202117022235.
Chinese Office Action dated Feb. 15, 2023 for App. No. 201980069963.8.

* cited by examiner

*Primary Examiner* — Yong L Chu
(74) *Attorney, Agent, or Firm* — K&L Gates LLP

(57) ABSTRACT

Compositions for regeneration of spent dialysis fluid are disclosed. The compositions include a sorbent comprising a titanium-glyoxal complex. Sorbent cartridges comprising the sorbents, and methods and systems for using the cartridges in dialysis also are disclosed.

21 Claims, 1 Drawing Sheet

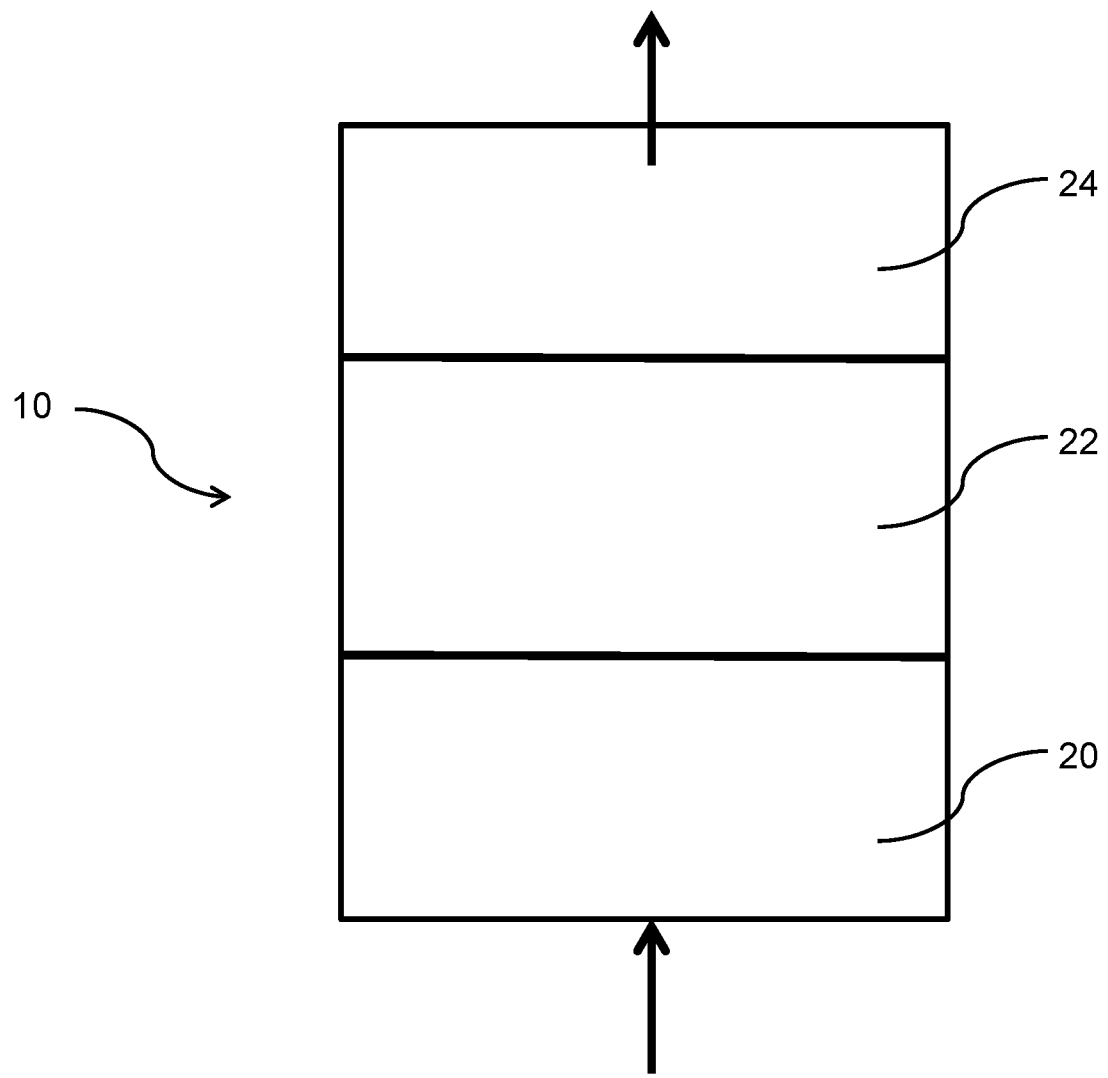

METHOD AND COMPOSITION FOR REMOVING UREMIC TOXINS

BACKGROUND

Field

The disclosure relates generally to dialysis processes, and more particularly to sorbents, cartridges containing the sorbents, and methods and systems for using the cartridges in dialysis.

Description of the Related Art

Disease, injury, or other factors can cause a person's renal system to fail. Renal failure leads to an imbalance of water and minerals (e.g., Na, K, Cl, Ca, P, Mg, $SO_4$) in the body, as well as impaired excretion of the daily metabolic load of fixed hydrogen ions. During renal failure, toxic end products of nitrogen metabolism including urea, creatinine, and uric acid can accumulate in the blood and tissues.

Dialysis processes have been devised for the separation of elements in a solution by diffusion across a semi-permeable membrane via a concentration gradient. Principally, dialysis in the United States comprises two methods: hemodialysis and peritoneal dialysis.

Hemodialysis ("HD") treatment utilizes the patient's blood, HD dialysis fluid, and a dialyzer to remove waste, toxins, and excess water from the patient. The patient is connected to a hemodialysis machine and the patient's blood is pumped through the dialyzer and back to the patient. Catheters are inserted into the patient's veins and arteries to allow blood flow to and from the dialyzer. Waste, toxins, and excess water are removed from the patient's blood into the HD dialysis fluid by diffusion and/or filtration and the blood is infused back into the patient. Hemodialysis treatments last several hours and are generally performed in a treatment center about three or four times per week, although some methods allowing overnight daily treatment at a patient's home have been proposed.

Peritoneal dialysis ("PD") uses a PD dialysis solution, which is infused into a patient's peritoneal cavity. The PD dialysis fluid contacts the patient's peritoneal membrane in the peritoneal cavity. Waste, toxins, and excess water pass from the patient's bloodstream through the peritoneal membrane and into the dialysis fluid during a specified dwell time via diffusion and osmosis. Spent dialysis fluid is then drained from the patient's peritoneal cavity to remove the waste, toxins, and water from the patient. The treatment can be repeated several times during the day or overnight, or both, to achieve the desired level of waste, toxin, and excess water removal.

During dialysis treatments, sorbents can be used to remove waste from the spent dialysis fluid, thereby regenerating the spent dialysis fluid for reuse. Dialysate regeneration advantageously reduces the overall volume of dialysis solution required for dialysis treatment. Sorbent materials include zirconium phosphate and zirconium oxide as ion exchange sorbents to remove cationic and/or anionic waste, and are disclosed, for example, in U.S. Patent Publication No. 2014/0001112. Other sorbent materials include a zirconium-glyoxal complex coated on activated carbon as described in U.S. Patent Publication No. 2014/0336568.

SUMMARY

In light of the disclosure herein, and without limiting the scope of the invention in any way, in a first embodiment of the present disclosure, which may be combined with any other embodiment listed herein unless specified otherwise, the disclosure provides a sorbent comprising titanium-glyoxal complex and a porous support material such as activated carbon.

In a second embodiment of the present disclosure, which may be combined with any other embodiment listed herein unless specified otherwise, the porous support material comprises activated carbon, graphene, graphene oxide, silicon, porous silicon, or a combination thereof.

In a third embodiment of the present disclosure, which may be combined with any other embodiment listed herein unless specified otherwise, the titanium-glyoxal complex comprises titanium-crosslinked hydrated glyoxal moieties.

In a fourth embodiment of the present disclosure, which may be combined with any other embodiment listed herein unless specified otherwise, the titanium-glyoxal complex is formed by reacting hydrated glyoxal with titanium ions.

In a fifth embodiment of the present disclosure, which may be combined with any other embodiment listed herein unless specified otherwise, the titanium-glyoxal complex has a structure comprising a molecule of formula I, formula II, formula III, formula IV, or a combination thereof:

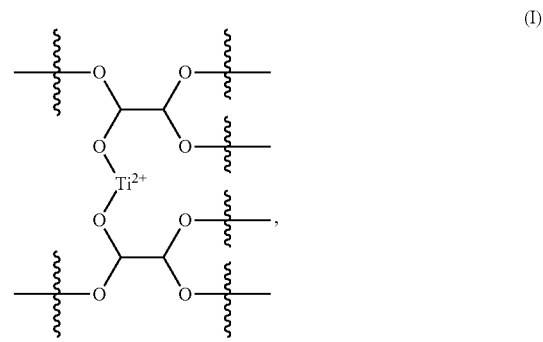

(I)

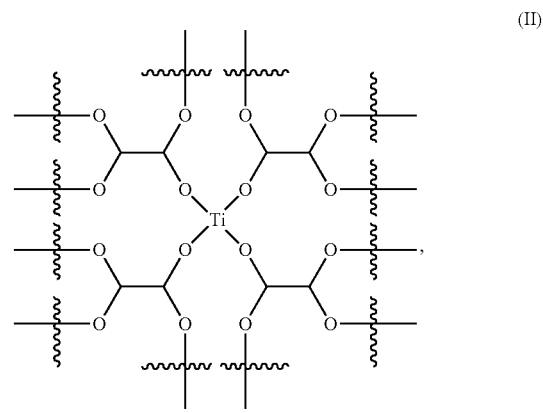

(II)

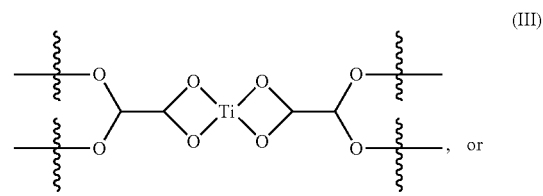

(III), or

-continued

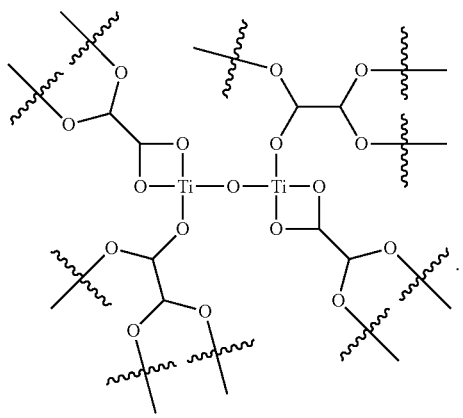

(IV)

In a sixth embodiment of the present disclosure, which may be combined with any other embodiment listed herein unless specified otherwise, the titanium-glyoxal complex is associated with, adhered to, adsorbed on, coated on, and/or immobilized on the porous support material such as activated carbon.

In a seventh embodiment of the present disclosure, which may be combined with any other embodiment listed herein unless specified otherwise, the titanium-glyoxal complex is present in pores of the porous support material such as activated carbon.

In an eighth embodiment of the present disclosure, which may be combined with any other embodiment listed herein unless specified otherwise, the sorbent has urea capacity of greater than about 50 mg urea/g sorbent, such as greater than about 60 mg/g, greater than about 70 mg/g, greater than about 75 mg/g, greater than about 80 mg/g, greater than about 90 mg/g, about 50 mg/g to about 200 mg/g, about 50 mg/g to about 150 mg/g, about 50 mg/g to about 100 mg/g, about 60 mg/g to about 100 mg/g, about 70 mg/g to about 90 mg/g, about 75 mg/g to about 85 mg/g, and/or about 80 mg/g.

In a ninth embodiment of the present disclosure, which may be combined with any other embodiment listed herein unless specified otherwise, the molar ratio of titanium to glyoxal is about 1:4.

In a tenth embodiment of the present disclosure, which may be combined with any other embodiment listed herein unless specified otherwise, the disclosure provides a sorbent cartridge comprising a sorbent according to any other embodiment listed herein.

In an eleventh embodiment of the present disclosure, which may be combined with any other embodiment listed herein unless specified otherwise, the sorbent cartridge is free of an immobilized urease layer.

In a twelfth embodiment of the present disclosure, which may be combined with any other embodiment listed herein unless specified otherwise, total content of active urease in the sorbent cartridge is less than about 5 wt. % based on total immobilized weight portion of cartridge contents.

In a thirteenth embodiment of the present disclosure, which may be combined with any other embodiment listed herein unless specified otherwise, the sorbent cartridge further comprises dialysate fluid which communicates with the sorbent. In an embodiment of the present disclosure, which may be combined with any other embodiment listed herein unless specified otherwise, the dialysate fluid has a pH of about 5 to about 9, such as about 5.5 to about 8.5, about 6 to about 8, about 6.1 to about 7.9, about 6.2 to about 7.8, about 6.3 to about 7.7, about 6.4 to about 7.6, about 6.5 to about 7.5, about 6.6 to about 7.4, about 6.7 to about 7.3, about 6.8 to about 7.2, about 6.9 to about 7.1, and/or about 7.

In a fourteenth embodiment of the present disclosure, which may be combined with any other embodiment listed herein unless specified otherwise, the sorbent cartridge further comprises a layer comprising titanium oxide, hydrous titanium dioxide, and/or titanium phosphate.

In a fifteenth embodiment of the present disclosure, which may be combined with any other embodiment listed herein unless specified otherwise, the disclosure provides a method comprising passing a fluid comprising urea though the sorbent according to any other embodiment listed herein and/or though the sorbent cartridge according to any other embodiment listed herein, thereby binding urea to the titanium-glyoxal complex. In an embodiment of the present disclosure, which may be combined with any other embodiment listed herein unless specified otherwise, the fluid comprising urea is a spent dialysis fluid. In an embodiment of the present disclosure, which may be combined with any other embodiment listed herein unless specified otherwise, the fluid comprising urea has a pH of about 5 to about 9, such as about 5.5 to about 8.5, about 6 to about 8, about 6.1 to about 7.9, about 6.2 to about 7.8, about 6.3 to about 7.7, about 6.4 to about 7.6, about 6.5 to about 7.5, about 6.6 to about 7.4, about 6.7 to about 7.3, about 6.8 to about 7.2, about 6.9 to about 7.1, and/or about 7.

In a sixteenth embodiment of the present disclosure, which may be combined with any other embodiment listed herein unless specified otherwise, the disclosure provides an apparatus for conducting dialysis comprising the sorbent cartridge according to any other embodiment listed herein, and a dialyzer in fluid communication with the sorbent cartridge, wherein spent dialysis fluid passes from the dialyzer to and through the sorbent cartridge. In an embodiment of the present disclosure, which may be combined with any other embodiment listed herein unless specified otherwise, the spent dialysis fluid is spent hemodialysis fluid or spent peritoneal dialysis fluid.

In a seventeenth embodiment of the present disclosure, which may be combined with any other embodiment listed herein unless specified otherwise, the dialyzer is in fluid communication with the blood of a patient.

In an eighteenth embodiment of the present disclosure, which may be combined with any other embodiment listed herein unless specified otherwise, the disclosure provides a dialysis system comprising the sorbent cartridge of any other embodiment listed herein and a source of spent dialysis fluid, wherein the source of spent dialysis fluid is in fluid communication with the sorbent cartridge and the spent dialysis fluid passes to and through the sorbent cartridge. In an embodiment of the present disclosure, which may be combined with any other embodiment listed herein unless specified otherwise, the spent dialysis fluid is spent hemodialysis fluid or spent peritoneal dialysis fluid.

In a nineteenth embodiment of the present disclosure, which may be combined with any other embodiment listed herein unless specified otherwise, the disclosure provides a method of making a sorbent for binding urea, comprising: (i) combining glyoxal, a titanium ion source, and a solvent to provide a mixture comprising a titanium-glyoxal complex; (ii) adding a porous support material to the mixture to provide a treated support material; (iii) separating the solvent from the treated support material; (iv) washing the treated support material to provide a washed treated support material; and (v) drying the washed treated support material to provide a sorbent for binding urea. In an embodiment of the present disclosure, which may be combined with any other embodiment listed herein unless specified otherwise, the porous support material comprises activated carbon, graphene, graphene oxide, silicon, porous silicon, or a combination thereof. In an embodiment of the present disclosure, which may be combined with any other embodiment listed herein unless specified otherwise, the disclosure provides a method of making a sorbent for binding urea, comprising: (i) combining glyoxal, a titanium ion source, and a solvent to provide a mixture comprising a titanium-glyoxal complex; (ii) adding activated carbon to the mixture to provide a treated activated carbon; (iii) separating the solvent from the treated activated carbon; (iv) washing the treated activated carbon to provide a washed treated activated carbon; and (v) drying the washed treated activated carbon to provide a sorbent for binding urea. In an embodiment of the present disclosure, which may be combined with any other embodiment listed herein unless specified otherwise, the drying step is carried out at a temperature of at least 25° C., such as at least 30° C., at least 35° C., at least 40° C., about 25° C. to about 40° C., about 30° C. to about 40° C., about 35° C. to about 40° C., and/or about 37° C.

In a twentieth embodiment of the present disclosure, which may be combined with any other embodiment listed herein unless specified otherwise, the titanium ion source is selected from the group consisting of titanium tetrachloride, titanium (II) chloride, titanium (III) chloride, titanium oxychloride, and combinations thereof.

In light of the disclosure and embodiments set forth herein, it is accordingly an advantage of the present disclosure to provide sorbents, sorbent cartridges, methods, and systems for dialysis processes that reduce or avoid generation of ammonia during urea removal.

It is another advantage of the present disclosure to efficiently adsorb urea at or near a physiological pH, eliminating the need to adjust the pH of the spent dialysis fluid before exposure to the sorbent material and of the purified or regenerated dialysate after exposure to the sorbent material.

Additional features and advantages of the disclosed formulations are described in, and will be apparent from, the following Detailed Description and the FIGURE. The features and advantages described herein are not all-inclusive and, in particular, many additional features and advantages will be apparent to one of ordinary skill in the art in view of the description. Also, any particular embodiment does not necessarily have to have all of the advantages listed herein. Moreover, it should be noted that the language used in the specification has been principally selected for readability and instructional purposes, and not to limit the scope of the inventive subject matter.

BRIEF DESCRIPTION OF THE FIGURES

FIG. 1 illustrates an embodiment of a cross-sectional view of a resin bed of a cartridge as disclosed herein.

DETAILED DESCRIPTION

Certain embodiments described herein relate generally to the field of dialysis processes. More particularly, some embodiments described herein relate to sorbents for use in dialysis processes to remove waste products such as uremic toxins that accumulate in dialysis fluids. Related embodiments described herein relate to cartridges containing the sorbents. Additional related embodiments described herein relate to methods and systems for using the cartridges in dialysis processes.

The sorbents, sorbent cartridges, methods, and systems described herein are useful for the removal of waste products (e.g., uremic toxins) that accumulate in dialysate fluids. The sorbent materials can be present in a container (e.g., one or more sorbent cartridges) capable of holding the sorbents useful for the removal process. The sorbents described in detail below, or the arrangement of sorbents, can be used in a dialysis system or other similar type of system that is useful for the removal of waste products that accumulate in dialysate fluids, for instance, as a result of conducting hemodialysis or peritoneal dialysis. As described in more detail below, the sorbents and sorbent cartridges are useful in purifying or regenerating dialysate used in hemodialysis and in peritoneal dialysis. Conventional dialysis solutions for peritoneal dialysis or hemodialysis can be used and can advantageously be regenerated by the described methods.

In one aspect, the sorbents, sorbent cartridges, methods and systems described herein are useful for removing uremic toxins from a patient by dialysis with non-enzymatic urea-binding sorbent materials. More specifically, the non-enzymatic urea-binding sorbent material can be used in one or more sorbent cartridges for dialysate regeneration or purification in dialysis. The sorbent cartridge(s) can be used for treatment of uremia and/or other conditions. Advantageously, the sorbent material and sorbent cartridge described herein can reduce or avoid generation of ammonia during urea removal because of the absence of enzymatic hydrolysis reactions of urea that are related to conventional use of urease. Additionally, a sorbent material comprising titanium described herein can efficiently adsorb urea at or near a physiological pH, eliminating the need to adjust the pH of the spent dialysis fluid before exposure to the sorbent material and of the purified or regenerated dialysis fluid after exposure to the sorbent material.

The sorbents disclosed herein comprise a titanium-glyoxal complex and a porous support material. The porous support material can comprise activated carbon, graphene, graphene oxide, silicon, porous silicon, or a combination thereof. The molar ratio of titanium to glyoxal in the sorbent can be about 1:4. The titanium-glyoxal complex can comprise titanium-crosslinked hydrated glyoxal moieties. For example, the titanium-glyoxal complex can have a structure comprising a molecule of formula I, formula II, formula III, formula IV, or a combination thereof:

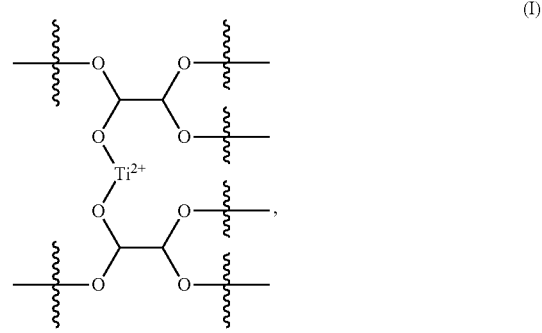

(I)

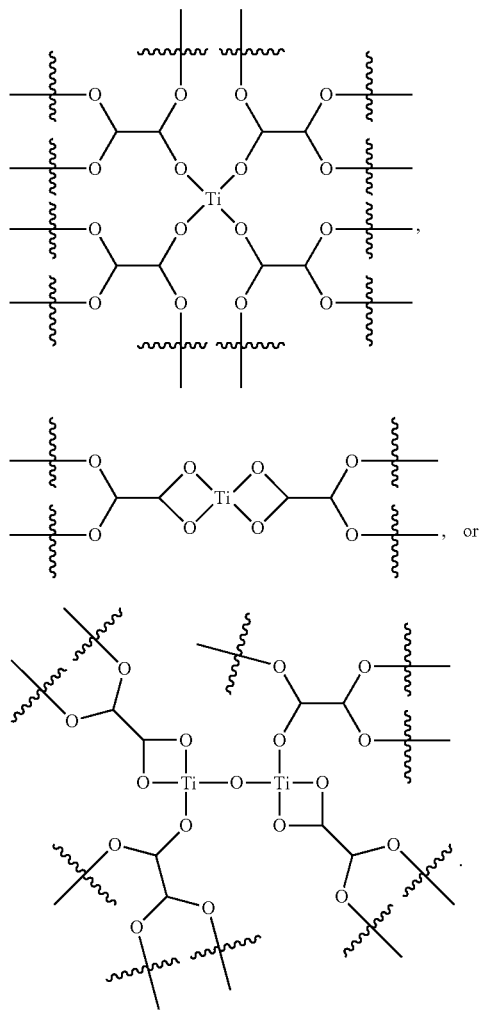

The titanium-glyoxal complex also includes titanium-glyoxal polymeric complexes having the structure Ti[hydrated glyoxal moiety]$_n$, wherein n is an integer from 2 to 10, such as from 2 to 8, from 2 to 6, from 3 to 5, or 4.

As used herein, the term "hydrated glyoxal" includes oligomeric and polymeric species of hydrated glyoxal, such as hydrated glyoxal dimers, hydrated glyoxal trimers, hydrated glyoxal oligomers, and hydrated glyoxal polymers.

The titanium-glyoxal complex described herein can be formed, for example, by reacting hydrated glyoxal with titanium ions. A urea-binding sorbent can be formed by treating a support material as described herein (e.g., activated carbon) with the titanium-glyoxal complex. The titanium-glyoxal complex can be associated with, adhered to, adsorbed on, and/or coated on the support material such as activated carbon. In some cases, the titanium-glyoxal complex is trapped within pores of the support material or otherwise immobilized to the support material, for example, the titanium-glyoxal complex is trapped within carbon pores or otherwise immobilized to the carbon. Urea-containing (e.g., spent) dialysate can be passed through a layer of the formed sorbent to complex urea with the sorbent, thereby purifying or regenerating the spent dialysis fluid.

The sorbents described herein are active toward urea adsorption and are capable of providing adequate urea binding capacity sufficient to eliminate the need for including an immobilized urease layer or similar-acting enzyme in the sorbent cartridge. As used herein, a cartridge "free of an immobilized urease layer" refers to the absence in the cartridge of any stationary continuous layer of urease extending across an internal cross-section thereof that is available for fluid flow. Further, the cartridge of the present invention can be substantially free or completely free of any active urease in the fluid flow compartment of the cartridge. For example, the total content of active urease in the fluid flow compartment of the cartridge can be less than about 5 wt % based on the total immobilized weight portion of the cartridge contents, for example, less than about 3 wt %, less than about 2 wt %, less than about 1 wt %, less than about 0.5 wt %, less than 0.1 wt %, and/or from 0 to about 5 wt % based on the total immobilized weight portion of the cartridge contents.

The sorbents described herein are capable of urea adsorption at or near physiological pH, which eliminates the need to acidify spent dialysis fluid entering the sorbent cartridge and to neutralize the regenerated dialysate exiting from the sorbent cartridge before the dialysate is reused in a dialyzer. In particular, due to the ability of the sorbents described herein to efficiently adsorb urea at or near physiological pH, the pH of dialysate fluid which communicates with the sorbent does not need to be adjusted (e.g., acidified) prior to reaction with the urea-binding sorbent, and thus also does not need to be restored to a neutral pH upon exiting the sorbent cartridge. The dialysis fluid which communicates with the sorbent can have a pH of about 5 to about 9, such as about 5.5 to about 8.5, about 6 to about 8, about 6.1 to about 7.9, about 6.2 to about 7.8, about 6.3 to about 7.7, about 6.4 to about 7.6, about 6.5 to about 7.5, about 6.6 to about 7.4, about 6.7 to about 7.3, about 6.8 to about 7.2, about 6.9 to about 7.1, and/or about 7. Similarly, the pH of the purified or regenerated dialysate fluid exiting the sorbent cartridge can have a pH of about 5 to about 9, such as about 5.5 to about 8.5, about 6 to about 8, about 6.1 to about 7.9, about 6.2 to about 7.8, about 6.3 to about 7.7, about 6.4 to about 7.6, about 6.5 to about 7.5, about 6.6 to about 7.4, about 6.7 to about 7.3, about 6.8 to about 7.2, about 6.9 to about 7.1, and/or about 7.

Activated carbon is one support material that, by itself, has very low adsorption capacity for urea but can be converted into an active urea sorbent, for example, by loading carbon with a titanium-glyoxal complex, such as glyoxal crosslinked by titanium. Activated carbon can be converted into a direct urea binding active material by treating carbon with a solution containing titanium-glyoxal complex. The glyoxal can be crosslinked with titanium ions to form a titanium crosslinked polymeric complex which can be trapped within carbon pores or otherwise immobilized to the carbon. The crosslinked titanium-glyoxal complex can be formed and trapped within the carbon pores, for example, upon drying of the treated carbon. When the treated carbon comes into contact with urea in spent dialysis fluid, the crosslinked titanium-glyoxal polymeric complex of the treated carbon can bind with the urea, which then is captured by the treated carbon.

When treated as indicated, the dried treated carbon becomes urea binding active and can attain urea adsorption capacity, such as greater than about 50 mg urea per g treated carbon, e.g., greater than about 60 mg/g, greater than about 70 mg/g, greater than about 75 mg/g, greater than about 80 mg/g, greater than about 90 mg/g, about 50 mg/g to about 200 mg/g, about 50 mg/g to about 150 mg/g, about 50 mg/g to about 100 mg/g, about 60 mg/g to about 100 mg/g, about 70 mg/g to about 90 mg/g, about 75 mg/g to about 85 mg/g, and/or about 80 mg/g. Urea-binding capacity can be measured in a column test by passing a dialysate containing urea through the column. The urea-binding carbons can avoid or reduce the indicated possible problems associated with sorbent material that uses the enzyme urease to convert the urea to ammonium carbonate, in a safe and possibly cost-reducing manner. The resultant urea binding carbon can be combined with additional titanium sorbents such as titanium phosphate, titanium oxide, and/or hydrous titanium dioxide in the form of a sorbent cartridge for sorbent regenerative dialysis to remove various uremic toxins from the patient (urea, creatinine, uric acid, phosphate, potassium, calcium etc.). Since no ammonium carbonate is produced as in a conventional sorbent cartridge using urease for the urea conversion, the regenerated dialysate is highly pure and uniform in composition allowing the dialysis system to be greatly simplified. Further, since the titanium-glyoxal complex can efficiently adsorb urea at physiological pH, pH adjustment of the spent dialysis fluid and of the purified or regenerated dialysate is minimal or not needed.

The urea-binding sorbent can be present as a layer (or layers) in a sorbent cartridge, and additional sorbents, including additional titanium sorbents such as titanium phosphate, titanium oxide, and/or hydrous titanium dioxide can be present as additional layers in the sorbent cartridge. The sorbent layer which comprises the urea-binding titanium-glyoxal complex can be used in an amount, for example, of from about 500 to about 2000 g per dialysis cartridge, such as from about 1000 to about 2000 g treated carbon per cartridge (or other amounts above or below these ranges) used in hemodialysis, or from about 750 to about 1250 g per cartridge (or other amounts above or below these ranges) used in peritoneal dialysis. Additional layers optionally can be included in the cartridge before, and/or after the sorbent layer comprising the titanium glyoxal complex, such as a layer comprising titanium oxide, a layer comprising titanium phosphate, and/or a layer comprising hydrous titanium dioxide.

The urea-binding sorbent described herein can be prepared by (i) combining glyoxal, a titanium ion source, and a solvent to provide a mixture comprising a titanium-glyoxal complex; and (ii) adding a porous support material such as activated carbon, graphene, graphene oxide, silicon, porous silicon, or a combination thereof to the mixture to provide a treated support material (e.g., a treated activated carbon). The titanium-glyoxal complex is thereby associated with, adhered to, adsorbed on, coated on, immobilized on, and/or present in pores of the support material such as activated carbon. The solvent can include, but is not limited to, water and organic solvents such as polar protic solvents and polar aprotic solvents. To obtain a sorbent material suitable for use in a sorbent cartridge, the solvent can be separated from the treated support material (e.g., the treated activated carbon), the treated support material (e.g., treated activated carbon) can be washed to provide a washed treated support material (e.g., a washed treated activated carbon); and/or the washed treated support material (e.g., washed, treated activated carbon) can be dried to provide a dried sorbent for binding urea. The solution for washing the treated support material (e.g., activated carbon) can include, but is not limited to water or acidic solutions, such as hydrochloric acid solutions (e.g., 3.5 N HCl solution). The titanium ion source can be titanium tetrachloride, titanium (II) chloride, titanium (III) chloride, titanium oxychloride, and combinations thereof. The drying step can be carried out at a temperature of at least 25° C., such as at least 30° C., at least 35° C., at least 40° C., about 25° C. to about 40° C., about 30° C. to about 40° C., about 35° C. to about 40° C., and/or about 37° C.

The sorbents and sorbent cartridges described herein can be used in a process for removing urea from a fluid, such as in a process that purifies and/or regenerates spent dialysis fluid, which also includes urea removal. The process can include passing a fluid comprising urea through the urea-binding sorbent and the sorbent cartridges containing a urea-binding sorbent as described herein, thereby binding urea to the titanium-glyoxal complex of the urea-binding sorbent. The process can comprise running spent (e.g., urea-containing) dialysis fluid through the sorbent or cartridge. The cartridge can comprise the titanium-glyoxal complex which is bound to a porous support material (e.g., activated carbon) in a sorbent layer. For example, the titanium-glyoxal complex can be associated with, adhered to, adsorbed on, coated on, immobilized on, and/or present in the pores of the support material (e.g., activated carbon). Spent dialysis fluid then can be passed through the sorbent layer loaded with the insolubilized titanium-glyoxal complex. The insolubilized titanium-glyoxal complex can be used as a urea binder itself, without need of additional urea binding materials. Additional layers through which the spent dialysis fluid passes optionally can be included in the cartridge before, and/or after the sorbent layer comprising the titanium glyoxal complex. Such layers can include a layer comprising titanium oxide, a layer comprising titanium phosphate, a layer comprising hydrous titanium dioxide, or a combination thereof, such as a layer comprising both titanium oxide and titanium phosphate. Such layers collectively comprise a resin bed of a cartridge as disclosed herein.

FIG. 1 illustrates an embodiment of a cross-sectional view of a resin bed 10 as disclosed herein. The resin bed 10 in the illustrated embodiment includes three layers 20, 22, and 24. The first layer 20 is a layer comprising titanium phosphate. The second layer 22 is a layer comprising titanium oxide. The third layer 24 is a layer comprising titanium-glyoxal complex. Fluid passes through the layers in the directed indicated by the arrows. Additional layers may be included in the sorbent cartridge and the layers in the sorbent cartridge may be provided in any order.

In the process for removing urea from a fluid to purify and/or regenerate spent dialysis fluid, the fluid, before contacting the urea-binding sorbent or entering the sorbent cartridge, can have a pH of about 5 to about 9, such as about 5.5 to about 8.5, about 6 to about 8, about 6.1 to about 7.9, about 6.2 to about 7.8, about 6.3 to about 7.7, about 6.4 to about 7.6, about 6.5 to about 7.5, about 6.6 to about 7.4, about 6.7 to about 7.3, about 6.8 to about 7.2, about 6.9 to about 7.1, and/or about 7. Further, after contacting the urea-binding sorbent or exiting the sorbent cartridge, the fluid can have a similar pH of about 5 to about 9, such as about 5.5 to about 8.5, about 6 to about 8, about 6.1 to about 7.9, about 6.2 to about 7.8, about 6.3 to about 7.7, about 6.4 to about 7.6, about 6.5 to about 7.5, about 6.6 to about 7.4, about 6.7 to about 7.3, about 6.8 to about 7.2, about 6.9 to about 7.1, and/or about 7.

The sorbents and sorbent cartridges described herein can be used in an apparatus for conducting dialysis, so as to purify and/or regenerate spent dialysis fluid. The apparatus can comprise a sorbent cartridge as described herein and a dialyzer in fluid communication with the sorbent cartridge, wherein spent dialysis fluid passes from the dialyzer to and through the sorbent cartridge. The spent dialysis fluid can be spent hemodialysate, spent peritoneal dialysate, spent hemofiltration fluid or spent diafiltration fluid. The dialyzer can be in fluid communication with the blood of a patient. The apparatus for conducting dialysis can be, for example, an apparatus for sorbent hemodialysis, a wearable artificial kidney, or an apparatus for sorbent peritoneal dialysis.

The sorbents and sorbent cartridges described herein can be used in a dialysis system, so as to purify and/or regenerate spent dialysis fluid. The dialysis system can comprise a sorbent cartridge as described herein and a source of spent dialysis fluid, wherein the source of spent dialysis fluid is in fluid communication with the sorbent cartridge and the spent dialysis fluid passes to and through the sorbent cartridge. The spent dialysis fluid can be spent hemodialysate, spent peritoneal dialysate, or others listed above. The spent dialysis fluid can pass through the sorbent cartridge at a rate, for example, of about 10 ml/min to about 1000 ml/min, about 100 ml/min to about 550 ml/min, and/or about 150 ml/min to about 400 ml/min. The dialysis system can regenerate the spent dialysis fluid without needing to adjust the pH of the spent dialysis fluid, and can regenerate the spent dialysis fluid to a pH level approximately equal to that of fresh dialysate. The system can also regenerate the spent dialysis fluid without the formation of ammonia.

EXAMPLES

Example 1

Preparation of Titanium-Glyoxal Complex

Titanium-glyoxal complex was prepared as shown in Scheme 1 by adding 4.87 g $TiCl_4$ (99% purity) to 15.28 g glyoxal (39% glyoxal in water). The mixture was stirred for about 20 minutes and the reaction flask was immersed in an ice bath as needed to obtain the titanium glyoxal complex in a mole ratio of $TiCl_4$:glyoxal of 1:4.

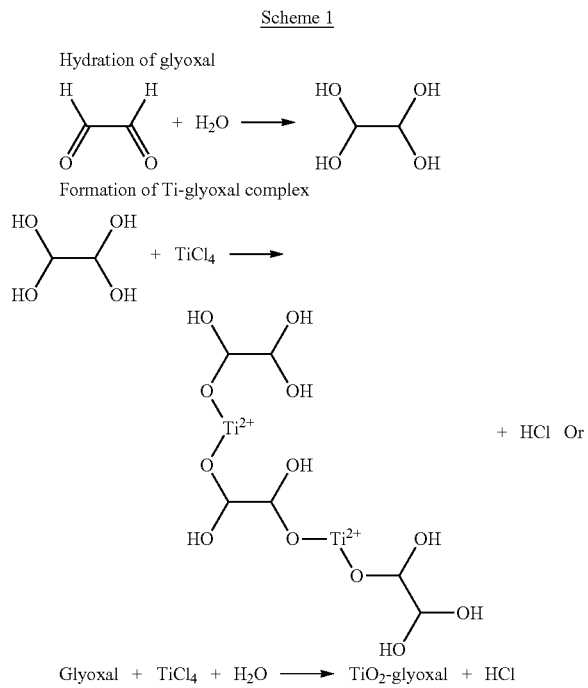

Scheme 1

Example 2

Preparation of Titanium-Glyoxal Complex on Activated Carbon

Activated carbon was coated with the titanium-glyoxal complex prepared according to Example 1 by adding about 10 g of the titanium-glyoxal solution to about 5 g of activated carbon (AC) as shown in Table 1:

TABLE 1

| Sample No. | Ti-glyoxal complex (g) | Activated carbon, CalgonCarbon, product: HPC SuperHD, 12 × 40 ("CC1") (g) | Activated carbon, CalgonCarbon, product: OLC AW, 12 × 40 ("CC2") (g) | Ti-Gly-AC final dry weight (g) |
|---|---|---|---|---|
| 1 | 9.438 | 5.0016 | — | 7.3527 |
| 2 | 10.562 | — | 5.036 | 6.7757 |

After soaking the titanium-glyoxal complex with the activated carbon for 3 hours, the mixture was washed twice with 40 ml 3.5 N HCl to remove excess titanium and glyoxal. The titanium-glyoxal coated activated carbon was filtered and dried at 37° C. for 22 hours, and then weighed to obtain the titanium-glyoxal-activated carbon (Ti-Gly-AC) final dry weight shown in Table 1.

Example 3

Urea Sorption by Titanium-Glyoxal-Activated Carbon

To measure urea sorption by the titanium-glyoxal complex-coated activated carbon, 1 g of each Ti-Gly-AC prepared according to Example 2 was added to a 50 mL centrifuge tube. Next, 50 ml of peritoneal dialysis (PD) solution containing urea (60 mg/dL or 257 mg/dL urea/PD solution) was added to the tubes. Each 100 ml of the DIANEAL® Low Calcium (2.5 mEq/L) Peritoneal Dialysis Solution with 2.5% Dextrose (catalog #5B9776) contains 2.5 g dextrose hydrous USP, 538 mg sodium chloride USP, 448 mg sodium lactate, 18.3 mg calcium chloride USP, and 5.08 mg magnesium chloride USP, and has a pH of about 5.2. The tubes were then rotated and liquid samples were collected from the tubes at different time points for urea, chemical analysis and pH.

Urea sorption capacity was calculated according to the following equation:

$$q=([BUN]_i-[BUN]_t)\times(60/28)\times V/100/S$$

in which:
q is urea capacity in mg urea/g sorbent
$[BUN]_i$ is concentration of BUN in dialysate solution at time 0 in mg/dL
$[BUN]_t$ is concentration of BUN in dialysate solution at time t in mg/dL
V is volume of test solution in ml
S is weight of sorbent in g.

A zirconium-glyoxal activated carbon sample was prepared by mixing 35 g of 39% glyoxal aqueous solution together with 75 ml of a 40% aqueous solution of zirconium (IV) oxychloride octahydrate ($ZrOCl \cdot 8H_2O$), then added 50 ml of 5N HCl solution and mixed overnight. Next, 55 mL of the resulting solution was mixed with 20 g of activated carbon for 4 hours, filtered with 150 ml of 3.5 N HCl and dried overnight in oven at 38° C.

As shown in Tables 2 and 3, the titanium-glyoxal complex-coated activated carbon demonstrated higher urea sorption capacity than either zirconium glyoxal complex-coated activated carbon or activated carbon alone. For example, as shown in Table 3, titanium-glyoxal coated on activated carbon demonstrated a urea capacity of 81.4 mg/g sorbent after 68 hours in a 257 mg/dL urea peritoneal dialysis (PD) solution at pH 4. In contrast, as shown in Table 2, urea capacity for zirconium-glyoxal on activated carbon was 373 mg/g sorbent for the same urea solution. Further, when rinsed with water (to bring the pH>2) zirconium-glyoxal coated on activated carbon had a urea capacity of 12.1 mg/kg (see Table 3), whereas water-rinsed titanium-glyoxal coated on activated carbon demonstrated a higher urea capacity of 41.4 g/kg sorbent after 68 hours in a 257 mg/dL urea peritoneal dialysis (PD) solution at pH 5 (see Table 3). Additionally, as shown in Table 3, titanium-glyoxal coated on activated carbon demonstrated a lower ammonia value compared to zirconium-glyoxal coated on activated carbon.

TABLE 2

| | | | | Original Zr-Gly-AC | | |
| | | | | | RUN 2 | RUN 1 |
| Tube | Sorbent | Test Solution | Time, hr | Urea capacity, mg/g sorbent | pH | Urea capacity, mg/g sorbent |
|---|---|---|---|---|---|---|
| 1 | Zr-Glyoxal-AC from CC1 | 257 mg/dL urea/PD | 0.5 | 16.3 | | |
| 1 | Zr-Glyoxal-AC from CC1 | 257 mg/dL urea/PD | 2 | 18.5 | | |
| 1 | Zr-Glyoxal-AC from CC1 | 257 mg/dL urea/PD | 67 | 34.4 | 2.24 | 37.3 |
| 1 | Zr-Glyoxal-AC from CC1 | 257 mg/dL urea/PD | 115 | | | 38.2 |
| 2 | Zr-Glyoxal-AC from CC2 | 257 mg/dL urea/PD | 0.5 | 15.3 | | |
| 2 | Zr-Glyoxal-AC from CC2 | 257 mg/dL urea/PD | 2 | 18.9 | | |
| 2 | Zr-Glyoxal-AC from CC2 | 257 mg/dL urea/PD | 67 | 34.2 | 2.46 | 39.3 |
| 2 | Zr-Glyoxal-AC from CC2 | 257 mg/dL urea/PD | 115 | | | 40.9 |
| 3 | Zr-Glyoxal-AC from GCC1 | 257 mg/dL urea/PD | 0.5 | 11.4 | | |
| 3 | Zr-Glyoxal-AC from GCC1 | 257 mg/dL urea/PD | 2 | 13.5 | | |
| 3 | Zr-Glyoxal-AC from GCC1 | 257 mg/dL urea/PD | 67 | 24.0 | 3.00 | 26.7 |
| 3 | Zr-Glyoxal-AC from GCC1 | 257 mg/dL urea/PD | 115 | | | 28.1 |
| 4 | AC from CC1 | 257 mg/dL urea/PD | 2 | 7.6 | | |
| 4 | AC from CC1 | 257 mg/dL urea/PD | 67 | 7.3 | 6.40 | |
| 5 | AC from CC2 | 257 mg/dL urea/PD | 2 | 7.1 | | |
| 5 | AC from CC2 | 257 mg/dL urea/PD | 67 | 6.9 | 8.36 | |
| 6 | AC from GCC1 | 257 mg/dL urea/PD | 2 | 7.8 | | |
| 6 | AC from GCC1 | 257 mg/dL urea/PD | 67 | 5.7 | 5.13 | |
| 7 | Zr-Glyoxal-AC from CC1 | 60 mg/dL urea/PD | 0.5 | 4.2 | | |
| 7 | Zr-Glyoxal-AC from CC1 | 60 mg/dL urea/PD | 2 | 5.3 | | |
| 7 | Zr-Glyoxal-AC from CC1 | 60 mg/dL urea/PD | 67 | 11.9 | 2.18 | 12.5 |
| 7 | Zr-Glyoxal-AC from CC1 | 60 mg/dL urea/PD | 115 | | | 14.3 |
| 8 | Zr-Glyoxal-AC from CC2 | 60 mg/dL urea/PD | 0.5 | 4.1 | | |
| 8 | Zr-Glyoxal-AC from CC2 | 60 mg/dL urea/PD | 2 | 5.7 | | |
| 8 | Zr-Glyoxal-AC from CC2 | 60 mg/dL urea/PD | 67 | 11.8 | 2.47 | 12.2 |
| 8 | Zr-Glyoxal-AC from CC2 | 60 mg/dL urea/PD | 115 | | | 13.7 |
| 9 | Zr-Glyoxal-AC from GCC1 | 60 mg/dL urea/PD | 0.5 | 3.1 | | |
| 9 | Zr-Glyoxal-AC from GCC1 | 60 mg/dL urea/PD | 2 | 4.0 | | |
| 9 | Zr-Glyoxal-AC from GCC1 | 60 mg/dL urea/PD | 67 | 9.1 | 2.54 | 8.5 |
| 9 | Zr-Glyoxal-AC from GCC1 | 60 mg/dL urea/PD | 115 | | | 10.1 |
| 10 | AC from CC1 | 60 mg/dL urea/PD | 2 | 2.3 | | |
| 10 | AC from CC1 | 60 mg/dL urea/PD | 67 | 2.0 | 6.10 | |
| 11 | AC from CC2 | 60 mg/dL urea/PD | 2 | 2.3 | | |
| 11 | AC from CC2 | 60 mg/dL urea/PD | 67 | 2.3 | 6.75 | |
| 12 | AC from GCC1 | 60 mg/dL urea/PD | 2 | 1.8 | | |
| 12 | AC from GCC1 | 60 mg/dL urea/PD | 67 | 2.0 | 6.18 | |

TABLE 3

| Sorbent | Test Solution | NH3, umol/L | BUN mg/dL | CA, mg/dL | Bicarb, mmol/L | Mg, mg/dL | P, mg/dL | Na, mmol/L | K, mmol/L | CL, mmol/L | pH | Urea, mg/dl | Urea capacity, mg/g sorbent |
|---|---|---|---|---|---|---|---|---|---|---|---|---|---|
| Zr-Glyoxal-AC from CC1 | 257 mg/dL urea/PD | 135.1 | 93 | 5.4 | 0.6 | 1.1 | 0 | 130 | 0.7 | 133 | 2.41 | 199.3 | 24.2 |
| Zr-Glyoxal-AC from CC2 | 257 mg/dL urea/PD | 476.9 | 90.6 | 4.7 | 0.3 | 0.6 | 0 | 130 | 0.8 | 125 | 2.9 | 194.1 | 27.8 |

TABLE 3-continued

| Sorbent | Test Solution | NH3, umol/L | BUN mg/dL | CA, mg/dL | Bicarb, mmol/L | Mg, mg/dL | P, mg/dL | Na, mmol/L | K, mmol/L | CL, mmol/L | pH | Urea, mg/dl | Urea capacity, mg/g sorbent |
|---|---|---|---|---|---|---|---|---|---|---|---|---|---|
| Ti-Glyoxal-AC from CC1 | 257 mg/dL urea/PD | 117.8 | 37.6 | 6.3 | 0.4 | 1.9 | 0 | 130 | 0.7 | 109 | 4 | 80.6 | 81.4 |
| Ti-Glyoxal-AC from CC2 | 257 mg/dL urea/PD | 259.9 | 56.4 | 5 | 0.2 | 1.3 | 0.1 | 131 | 1.5 | 110 | 3.9 | 120.9 | 63.0 |
| Zr-Glyoxal-AC CC1 rinsed | 257 mg/dL urea/PD | 66 | 105.9 | 4.1 | 0.3 | 0.6 | 0 | 131 | 0.7 | 97 | 4.79 | 226.9 | 12.1 |
| Zr-Glyoxal-AC CC2 rinsed | 257 mg/dL urea/PD | 76.1 | 106 | 4.3 | 0 | 0.6 | 0 | 132 | 0.7 | 97 | 5.04 | 227.1 | 11.9 |
| Ti-Glyoxal-AC CC1 rinsed | 257 mg/dL urea/PD | 108.5 | 77.6 | 4.9 | 0.5 | 1.2 | 0 | 131 | 0.7 | 99 | 5.01 | 166.3 | 41.4 |
| Ti-Glyoxal-AC CC2 rinsed | 257 mg/dL urea/PD | 246.6 | 17.7 | 5.4 | 0.1 | 1.1 | 0 | 131 | 0.7 | 113 | 4.83 | 37.9 | 99.7 |
| Zr-Glyoxal-AC from CC1 | 60 mg/dL urea/PD | 729 | 18.3 | 4.7 | 0.4 | 0.6 | 0 | 131 | 0.8 | 126 | 2.58 | 39.2 | 9.8 |
| Zr-Glyoxal-AC from CC2 | 60 mg/dL urea/PD | 711 | 18.9 | 4.6 | 0.4 | 0.6 | 0 | 131 | 0.8 | 127 | 2.73 | 40.5 | 9.2 |
| Ti-Glyoxal-AC from CC1 | 60 mg/dL urea/PD | 138.3 | 6 | 6.2 | 0.4 | 1.9 | 0.1 | 131 | 0.7 | 110 | 3.84 | 12.9 | 22.6 |
| Ti-Glyoxal-AC from CC2 | 60 mg/dL urea/PD | 334.8 | 9.5 | 5 | 0.5 | 1.3 | 0.1 | 132 | 1.6 | 111 | 3.78 | 20.4 | 18.7 |
| Zr-Glyoxal-AC CC1 rinsed | 60 mg/dL urea/PD | 118.5 | 23.6 | 4.1 | 0.5 | 0.6 | 0 | 131 | 0.7 | 97 | 4.58 | 50.6 | 4.4 |
| Zr-Glyoxal-AC CC2 rinsed | 60 mg/dL urea/PD | 115.7 | 24.4 | 4.3 | 0 | 0.6 | 0 | 132 | 0.7 | 96 | 4.68 | 52.3 | 3.6 |
| Ti-Glyoxal-AC CC1 rinsed | 60 mg/dL urea/PD | 94.8 | 11.7 | 5.4 | 0.3 | 1.8 | 0 | 132 | 0.7 | 99 | 5.08 | 25.1 | 16.7 |
| Ti-Glyoxal-AC CC2 rinsed | 60 mg/dL urea/PD | 149.5 | 17 | 4.5 | 0 | 0.9 | 0 | 131 | 0.7 | 98 | 4.75 | 36.4 | 11.1 |
|  | 257 mg/dL urea/PD | 4.1 | 117.4 | 4.7 | 0.1 | 0.6 | 0 | 132 | 0.7 | 93 |  | 251.6 |  |
|  | 257 mg/dL urea/PD | 4.5 | 117.9 | 4.7 | 0 | 0.6 | 0 | 132 | 0.7 | 93 |  | 252.6 |  |
|  | 60 mg/dl urea/PD | 2 | 28.1 | 4.6 | 0.2 | 0.6 | 0 | 130 | 0.7 | 92 |  | 60.2 |  |
|  | 60 mg/dl urea/PD | 4.1 | 27.6 | 4.7 | 0 | 0.6 | 0 | 131 | 0.7 | 93 |  | 59.1 |  |

Example 4

Urea Sorption by Titanium-Glyoxal-Activated Carbon at Neutral pH

To measure urea sorption by the titanium-glyoxal complex-coated activated carbon, 1 g of Ti-Gly-AC prepared according to Example 2 was added to a 50 mL centrifuge tube. Next, 50 ml of 112 mg/dL urea nitrogen dialysis solution was added to the tube. The dialysis solution contains: 112 mg/dL BUN, 0.2 mg/dL $Ca^{2+}$, 17 mmol/L bicarbonate, 2.6 mg/dL $Mg^{2+}$, 3.1 mg/dL phosphorous, 130 mmol/L $Na^+$, 3.2 mmol/L $K^+$, and 113 mmol/L $Cl^-$, and is at pH 8.8. Samples that were rinsed, were rinsed with RO water, filtered, and dried at 37° C. The tubes were then rotated and liquid samples were collected from the tubes at different time points for urea, electrolyte analysis and pH.

Urea sorption capacity was calculated according to the following equation:

$$q=([BUN]_i-[BUN]_t)\times(60/28)\times V/100/S$$

in which:
q is urea capacity in mg urea/g sorbent
$[BUN]_i$ is concentration of BUN in dialysate solution at time 0 in mg/dL
$[BUN]_t$ is concentration of BUN in dialysate solution at time t in mg/dL
V is volume of test solution in ml
S is weight of sorbent in g.

Zirconium glyoxal complex-coated activated carbon was prepared as described in Example 3.

As shown in Table 4, the titanium-glyoxal complex-coated activated carbon demonstrated higher urea sorption capacity than either zirconium glyoxal complex-coated activated carbon or activated carbon alone. For example, titanium-glyoxal coated on activated carbon demonstrated a urea capacity of 58 mg/g sorbent after 68 hours in a 112 mg/dL urea nitrogen dialysate solution around pH 7. In contrast, urea capacity for zirconium-glyoxal on activated carbon was 11 mg/g sorbent for the same urea solution.

TABLE 4

| Sorbent | Time, hr. | NH3, umol/L | BUN, mg/dL | CA, mg/dL | Bicarb, mmol/L | Mg, mg/dL | P, mg/dL | Na, mmol/L | K, mmol/L | CL, mmol/L | pH | Avg Urea capacity, mg/g sorbent |
|---|---|---|---|---|---|---|---|---|---|---|---|---|
| Zr-Glyoxal-AC from CC1 | 0.5 | 88.9 | 102.1 | 1 | 0.2 | 3.2 | 1.4 | 129 | 3.2 | 145 | | 10.2 |
| Zr-Glyoxal-AC from CC1 | 68 | 79.1 | 96.4 | 1.2 | 0.2 | 3.3 | 0 | 128.5 | 3.2 | 148 | 2.1 | 17.0 |
| Ti-Glyoxal-AC from CC1-new1 | 0.5 | 16.8 | 101.1 | 0.4 | 4.1 | 2.7 | 1.9 | 130 | 3.2 | 127 | | 11.1 |
| Ti-Glyoxal-AC from CC1-new1 | 68 | 38.9 | 17.3 | 0.5 | 0.2 | 2.7 | 0.7 | 129.5 | 3.2 | 129.5 | 4.8 | 98.6 |
| ZR-Glyoxal-AC CC1 rinsed | 0.5 | 9.6 | 102.2 | 0.2 | 13.6 | 2.2 | 2 | 129 | 3.1 | 114 | | 10.1 |
| ZR-Glyoxal-AC CC1 rinsed | 68 | 23.9 | 101.8 | 0.2 | 11.4 | 1.7 | 0.2 | 128 | 3.1 | 114.5 | 7.4 | 11.4 |
| Ti-Glyoxal-AC-new1-rinse | 0.5 | 22.6 | 102.1 | 0.2 | 12.9 | 2.5 | 2.5 | 128 | 3.1 | 114 | | 10.2 |
| Ti-Glyoxal-AC-new1-rinse | 68 | 67.2 | 57.3 | 0.2 | 10.3 | 2.5 | 1.8 | 129.5 | 3.2 | 115.5 | 7.2 | 58.3 |
| AC from CC1 | 0.5 | 3.8 | 100.7 | 0.4 | 18.2 | 2.4 | 2.9 | 130 | 3.2 | 112 | | 11.7 |
| AC from CC1 | 68 | 7.4 | 100.5 | 0.6 | 18.5 | 2.3 | 2.5 | 130 | 3.2 | 111.5 | 9.2 | 12.8 |

While the above is a complete description of the preferred embodiments of the invention, various alternatives, modifications, and equivalents may be used. Therefore, the above description should not be taken as limiting the scope of the invention which is defined by the appended claims.

What is claimed is:

1. A sorbent comprising a titanium-glyoxal complex and a porous support material including at least one of activated carbon, graphene, graphene oxide, non-porous silicon, porous silicon, or a combination thereof, wherein the titanium-glyoxal complex is configured to absorb urea, and wherein the sorbent comprising the titanium-glyoxal complex and the porous support material demonstrates a urea sorption at least two times higher than that of another sorbent comprising zirconium-glyoxal on activated carbon under the same urea sorption assay condition.

2. The sorbent of claim 1, wherein the porous support material comprises pores for holding the titanium-glyoxal complex inside the pores.

3. The sorbent of claim 1, wherein the titanium-glyoxal complex comprises titanium-crosslinked hydrated glyoxal moieties.

4. The sorbent of claim 1, wherein the titanium-glyoxal complex is formed by reacting hydrated glyoxal with titanium ions.

5. The sorbent of claim 1, wherein the titanium-glyoxal complex has a structure comprising a molecule of formula I, formula II, formula III, formula IV, or a combination thereof:

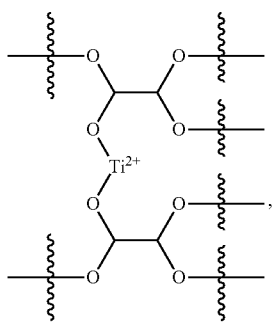

(I)

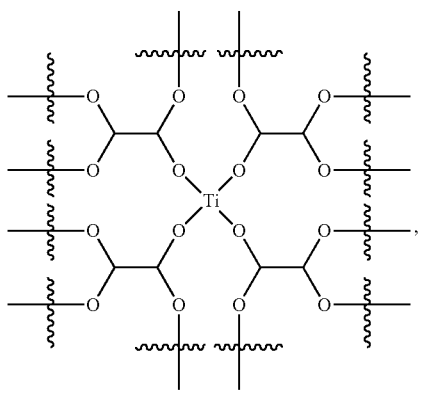

(II)

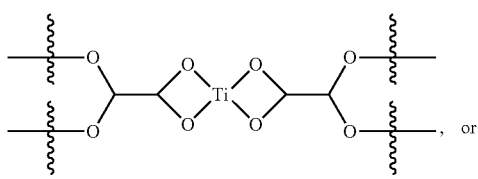

(III)

, or

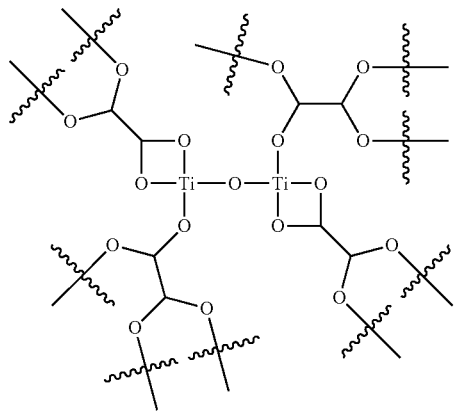

(IV)

6. The sorbent of claim 1, wherein the titanium-glyoxal complex is associated with, adhered to, adsorbed on, coated on, and/or immobilized on the porous support material.

7. The sorbent of claim 1, wherein the titanium-glyoxal complex is present in pores of the porous support material.

8. The sorbent of claim 1, which includes a urea sorption capacity of greater than 50 mg urea/g sorbent.

9. The sorbent of claim 1, wherein the molar ratio of titanium to glyoxal is 1:4.

10. A sorbent cartridge comprising the sorbent of claim 1.

11. The sorbent cartridge of claim 10, wherein the sorbent cartridge is free of an immobilized urease layer.

12. The sorbent cartridge of claim 10, wherein total content of active urease in the cartridge is less than about 5 wt. % based on total immobilized weight portion of cartridge contents.

13. The sorbent cartridge of claim 10, further comprising dialysate fluid which communicates with the sorbent.

14. The sorbent cartridge of claim 10, further comprising a layer comprising titanium oxide, hydrous titanium dioxide, and/or titanium phosphate.

15. A method comprising passing a fluid comprising urea though the sorbent of claim 1 and/or through the sorbent cartridge of claim 10, thereby binding urea to the titanium-glyoxal complex.

16. An apparatus for conducting dialysis comprising the sorbent cartridge of claim 10, and a dialyzer in fluid communication with the sorbent cartridge, wherein spent dialysis fluid passes from the dialyzer to and through the sorbent cartridge.

17. A dialysis system comprising the sorbent cartridge of claim 10 and a source of spent dialysis fluid, wherein the source of spent dialysis fluid is in fluid communication with the sorbent cartridge and the spent dialysis fluid passes to and through the sorbent cartridge.

18. A method of making a sorbent of claim 1 for binding urea, comprising:
(i) combining glyoxal, a titanium ion source, and a solvent to provide a mixture comprising a titanium-glyoxal complex;
(ii) adding activated carbon to the mixture to provide a treated activated carbon;
(iii) separating the solvent from the treated activated carbon; and
(iv) washing the treated activated carbon to provide a washed treated activated carbon;
(v) drying the washed treated activated carbon to provide a sorbent for binding urea.

19. A sorbent comprising a titanium-glyoxal complex and a porous support material, the titanium-glyoxal complex comprising titanium-glyoxal polymeric complexes having the structure Ti[hydrated glyoxal moiety]$_n$, wherein n is an integer from 2 to 10, and the porous support material comprising at least one of activated carbon, graphene, graphene oxide, non-porous silicon, porous silicon, or a combination thereof, wherein the titanium-glyoxal complex is configured to absorb urea, and wherein the sorbent comprising the titanium-glyoxal complex and the porous support material demonstrates a urea sorption at least two times higher than that of another sorbent comprising zirconium-glyoxal on activated carbon under the same urea sorption assay condition.

20. The sorbent of claim 1, wherein the porous support material comprises the activated carbon.

21. The sorbent of claim 19, wherein the porous support material comprises the activated carbon.

\* \* \* \* \*